United States Patent
Djunaedi et al.

(10) Patent No.: US 8,972,020 B2
(45) Date of Patent: Mar. 3, 2015

(54) COIL CABLE FOR AN IMPLANTABLE MEDICAL DEVICE

(71) Applicants: Ferdie Josef Djunaedi, Sydney (AU); Tad Jurkiewicz, Sydney (AU)

(72) Inventors: Ferdie Josef Djunaedi, Sydney (AU); Tad Jurkiewicz, Sydney (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/795,001

(22) Filed: Mar. 12, 2013

(65) Prior Publication Data
US 2014/0277275 A1    Sep. 18, 2014

(51) Int. Cl.
*A61N 1/00*    (2006.01)
*A61N 1/36*    (2006.01)

(52) U.S. Cl.
CPC .................................. *A61N 1/36032* (2013.01)
USPC ................................ 607/57; 607/55; 607/137

(58) Field of Classification Search
CPC .......................... A61N 1/0541; A61N 1/36032
USPC ............................... 607/55, 136, 137, 149, 57
See application file for complete search history.

(56) References Cited

U.S. PATENT DOCUMENTS

| | | | |
|---|---|---|---|
| 6,560,488 | B1 | 5/2003 | Crawford |
| 7,860,572 | B2 | 12/2010 | Ibrahim |
| 2007/0106344 | A1* | 5/2007 | Darley et al. .................. 607/55 |
| 2010/0124346 | A1 | 5/2010 | Higgins |
| 2012/0014549 | A1 | 1/2012 | Higgins |
| 2012/0041517 | A1 | 2/2012 | Walsh et al. |

FOREIGN PATENT DOCUMENTS

WO    2010099581 A1    9/2010

* cited by examiner

*Primary Examiner* — Allen Porter, Jr.
(74) *Attorney, Agent, or Firm* — Edell, Shapiro & Finnan, LLC

(57) ABSTRACT

Presented herein is a shapeable coil cable for use in connection with an implantable medical device comprising first and second external components. The shapeable coil cable is a conformable and non-resilient member that is sufficiently pliable to accept a configuration set by a user and sufficiently rigid to retain the configuration set by the user.

12 Claims, 13 Drawing Sheets

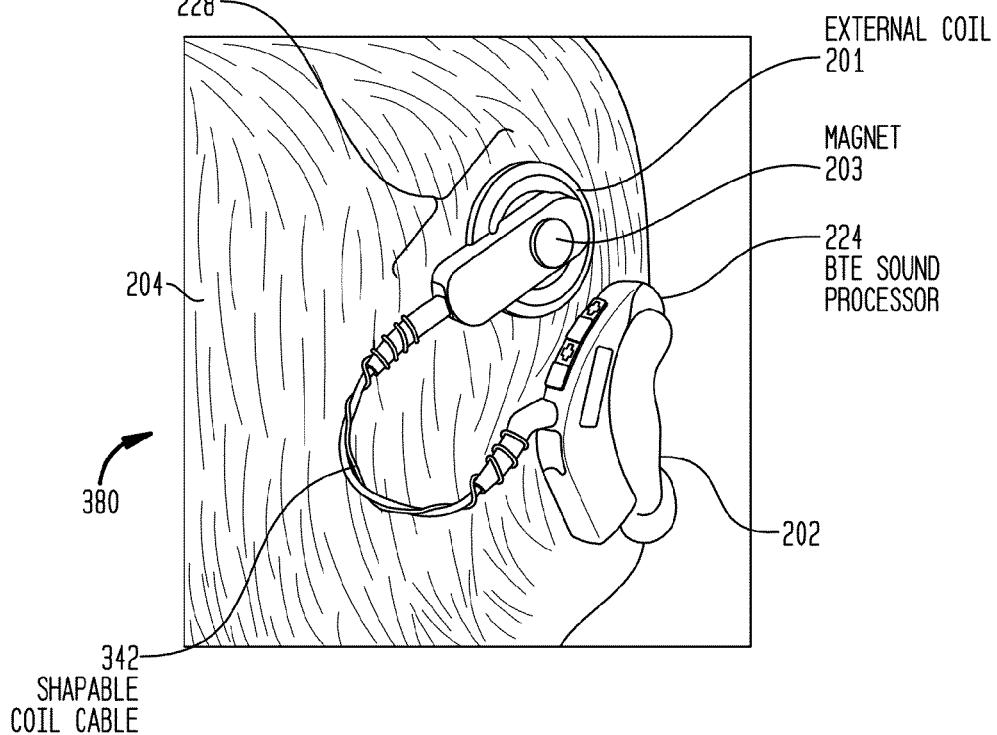
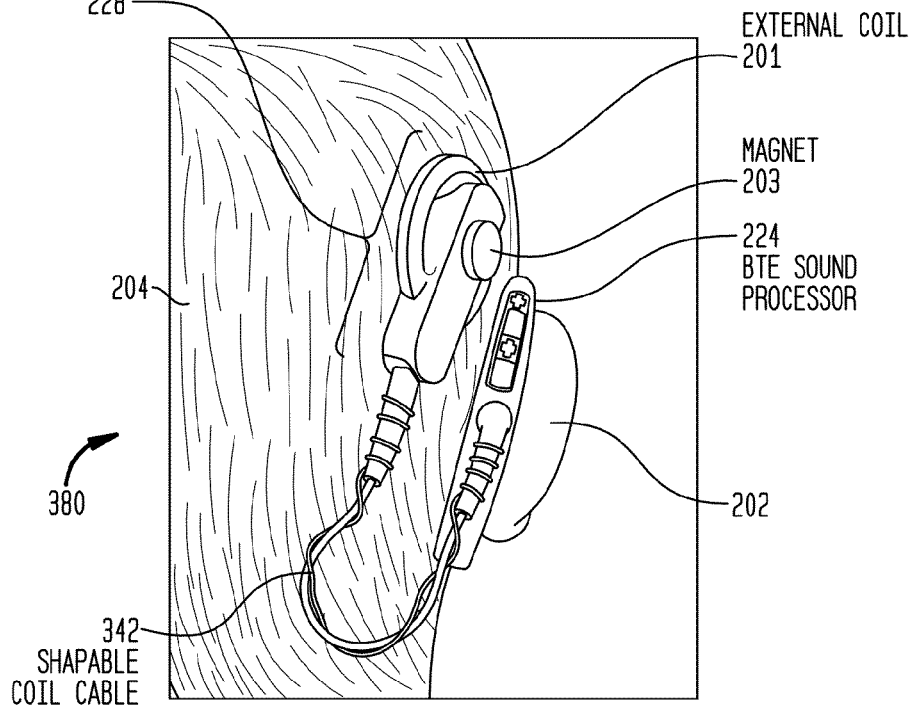

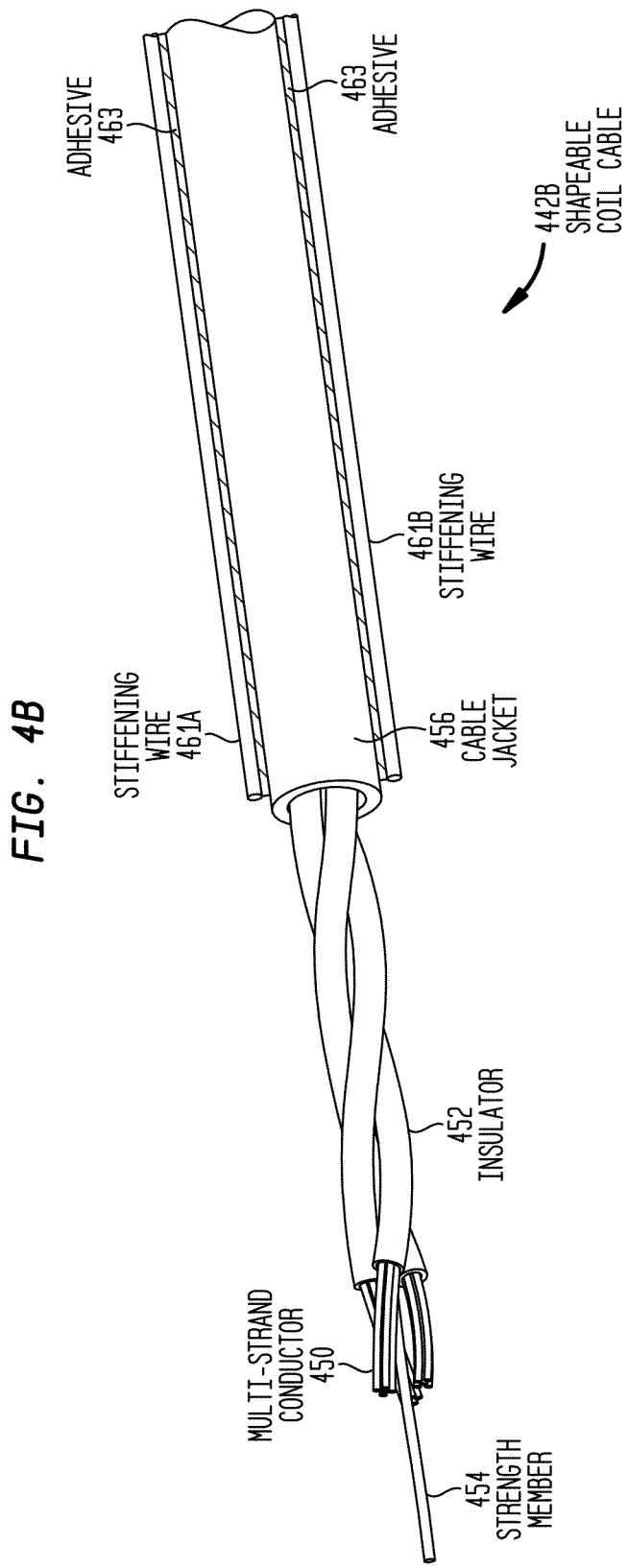

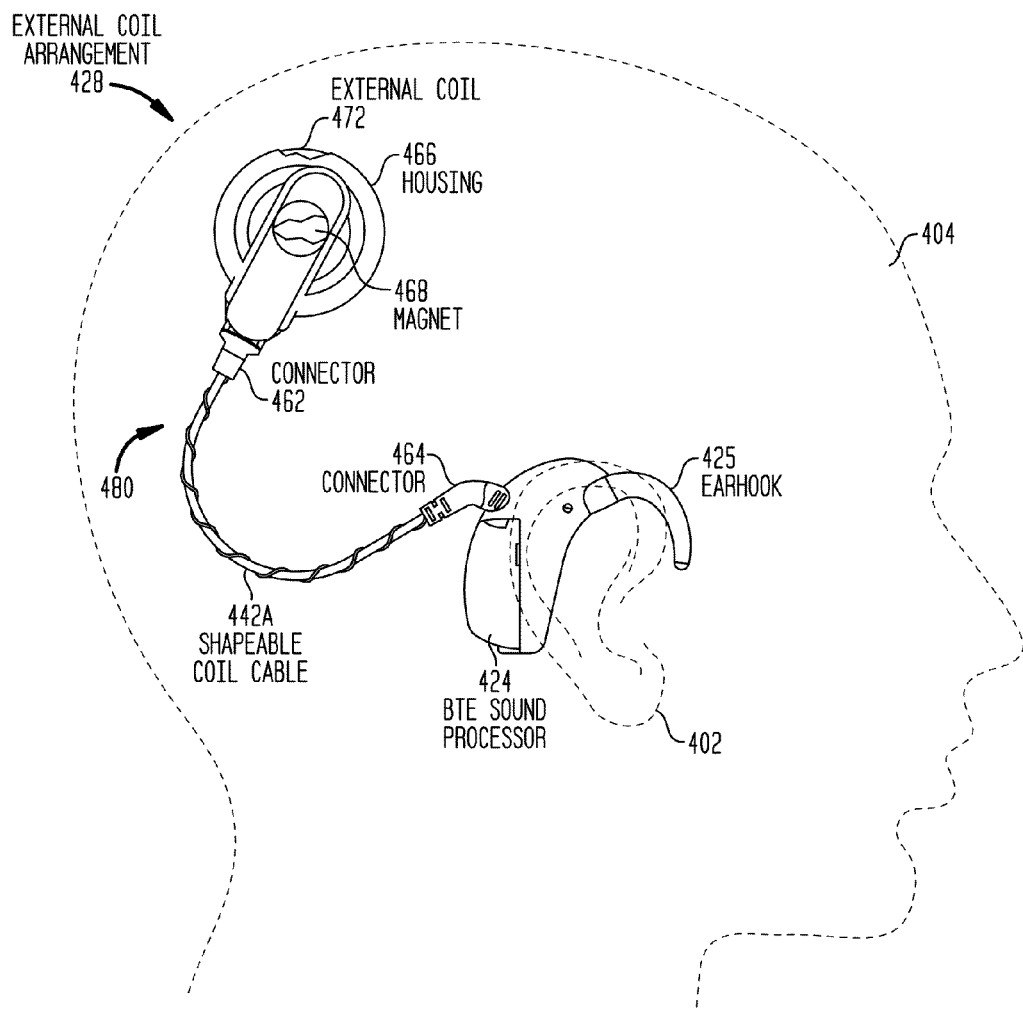

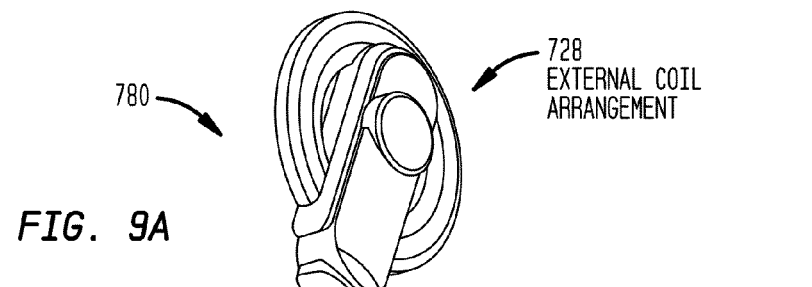
FIG. 9A
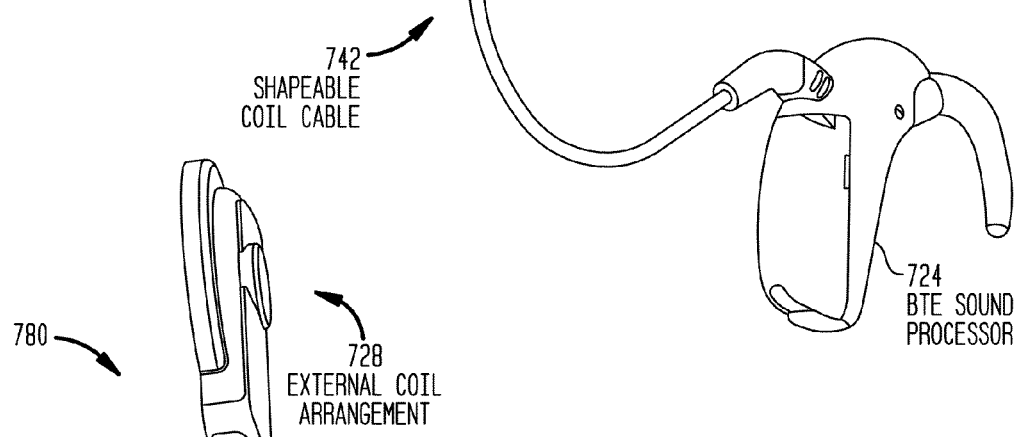
FIG. 9B
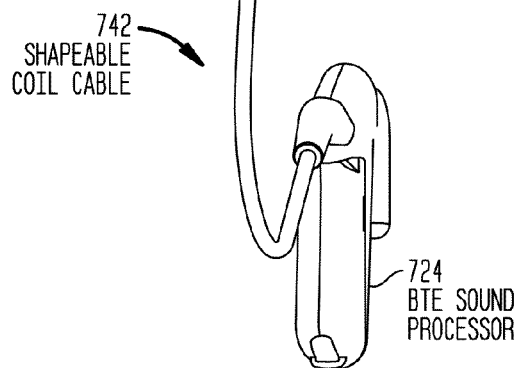

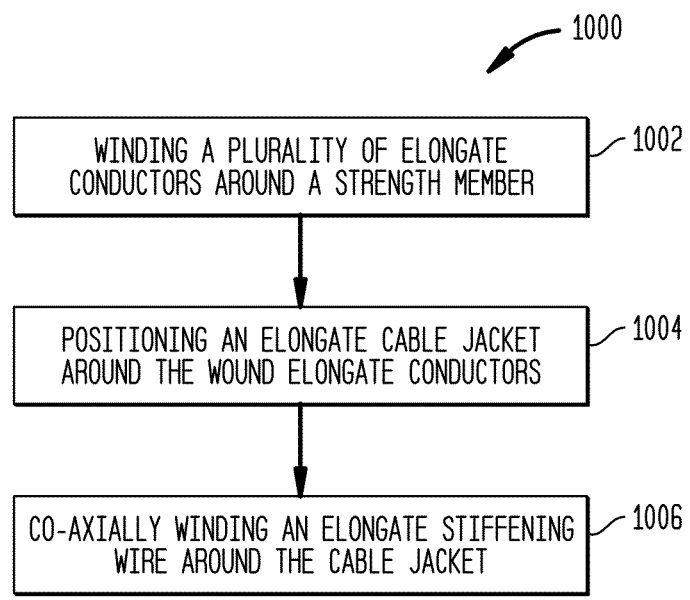

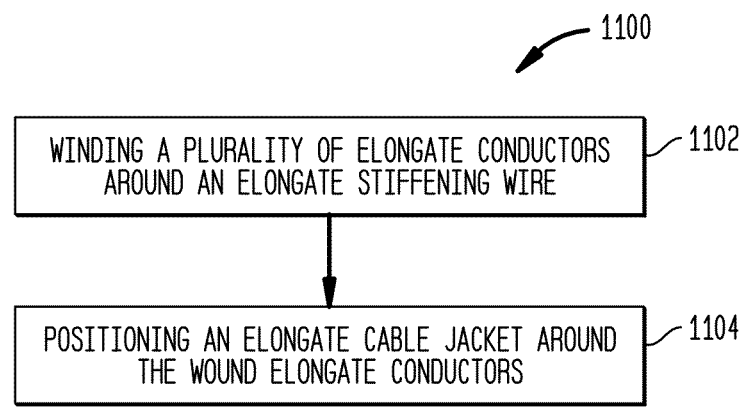

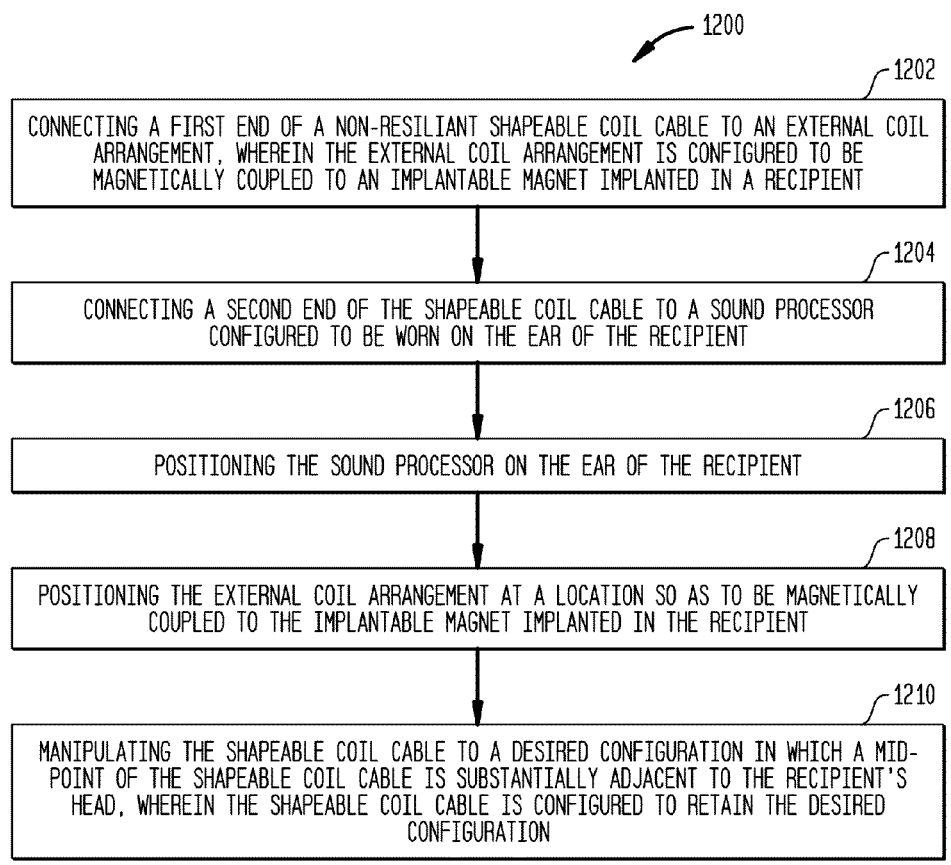

COIL CABLE FOR AN IMPLANTABLE MEDICAL DEVICE

BACKGROUND

1. Field of the Invention

The present invention relates generally to implantable medical devices, and more particularly, to a coil cable for an implantable medical device.

2. Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing life saving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify of the anatomy or of a physiological process. Many of these functional components utilize power and/or data received from external components that are part of, or operate in conjunction with, the implantable medical device.

SUMMARY

In one aspect of the invention, an apparatus is provided. The apparatus comprises a first external element configured to be worn by a recipient, a second external element, and a non-resilient shapeable cable configured to maintain an electrical connection between the first and second external elements.

In another aspect of the invention, a hearing prosthesis is provided. The hearing prosthesis comprises an implantable component configured to be implanted in a recipient and an external component. The external component comprises a sound processor configured to be worn by a recipient, an external coil arrangement, and a non-resilient shapeable cable configured to maintain an electrical connection between the sound processor and the external coil arrangement, wherein the shapeable cable has sufficient pliability to accept a configuration set by a user and sufficient rigidity to retain the configuration.

In a further aspect of the present invention, a method is provided. The method comprises connecting a first end of a non-resilient shapeable coil cable to an external coil arrangement, wherein the external coil arrangement is configured to be magnetically coupled to an implantable magnet implanted in a recipient. The method also comprises connecting a second end of the shapeable coil cable to a sound processor configured to be worn on the ear of the recipient. The method further comprises positioning the sound processor on the ear of the recipient, positioning the external coil arrangement at a location so as to be magnetically coupled to the implantable magnet implanted in the recipient, and manipulating the shapeable coil cable to a desired configuration in which a mid-point of the shapeable coil cable is substantially adjacent to the recipient's head, wherein the shapeable coil cable is configured to retain the desired configuration.

BRIEF DESCRIPTION OF THE DRAWINGS

Embodiments of the present invention are described herein in conjunction with the accompanying drawings, in which:

FIGS. 3A and 3B are perspective views of an external component of a cochlear implant that includes a shapeable coil cable in accordance with embodiments of the present invention;

FIG. 4B is a perspective view of a shapeable coil cable in accordance with alternative embodiments of the present invention;

FIG. 5 is a side view of an external component of a cochlear implant that comprises a shapeable coil cable in accordance with embodiments of the present invention;

FIGS. 9A and 9B are perspective views of the external component of FIG. 8;

FIG. 10 is a flowchart of a method in accordance with embodiments of the present invention;

FIG. 11 is a flowchart of another method in accordance with embodiments of the present invention; and FIG. 12 is a flowchart of a further method in accordance with embodiments of the present invention.

DETAILED DESCRIPTION

Embodiments of the present invention are generally directed to a shapeable coil cable for use in connection with an implantable medical device comprising first and second external elements. The shapeable coil cable is conformable, non-resilient and configured to maintain an electrical connection between the first and second external elements. That is, the shapeable coil cable is sufficiently pliable to accept a configuration set by a user and sufficiently rigid to retain the configuration set by the user.

There are different types of implantable medical devices having a wide variety of corresponding implantable components that may be partially or fully implanted into a recipient. For example, implantable medical devices may include hearing prostheses (e.g., auditory brain stimulators, bone conduction devices, mechanical stimulators, cochlear implants, etc.), sensors, implantable pacemakers, defibrillators, functional electrical stimulation devices, catheters, etc. Many of these implantable medical devices utilize power and/or data received from external components that are part of, or operate in conjunction with, the implantable medical device. It is to be appreciated that a shapeable coil cable in accordance with embodiments of the present invention may be used in connection with any of the above or other implantable medical devices. However, merely for ease of description, embodiments of the coil retention systems are primarily described herein in connection with one exemplary implantable medical device, namely a cochlear implant (also commonly referred to as cochlear implant device, cochlear prosthesis, and the like; simply "cochlear implant" herein).

Figure 1:
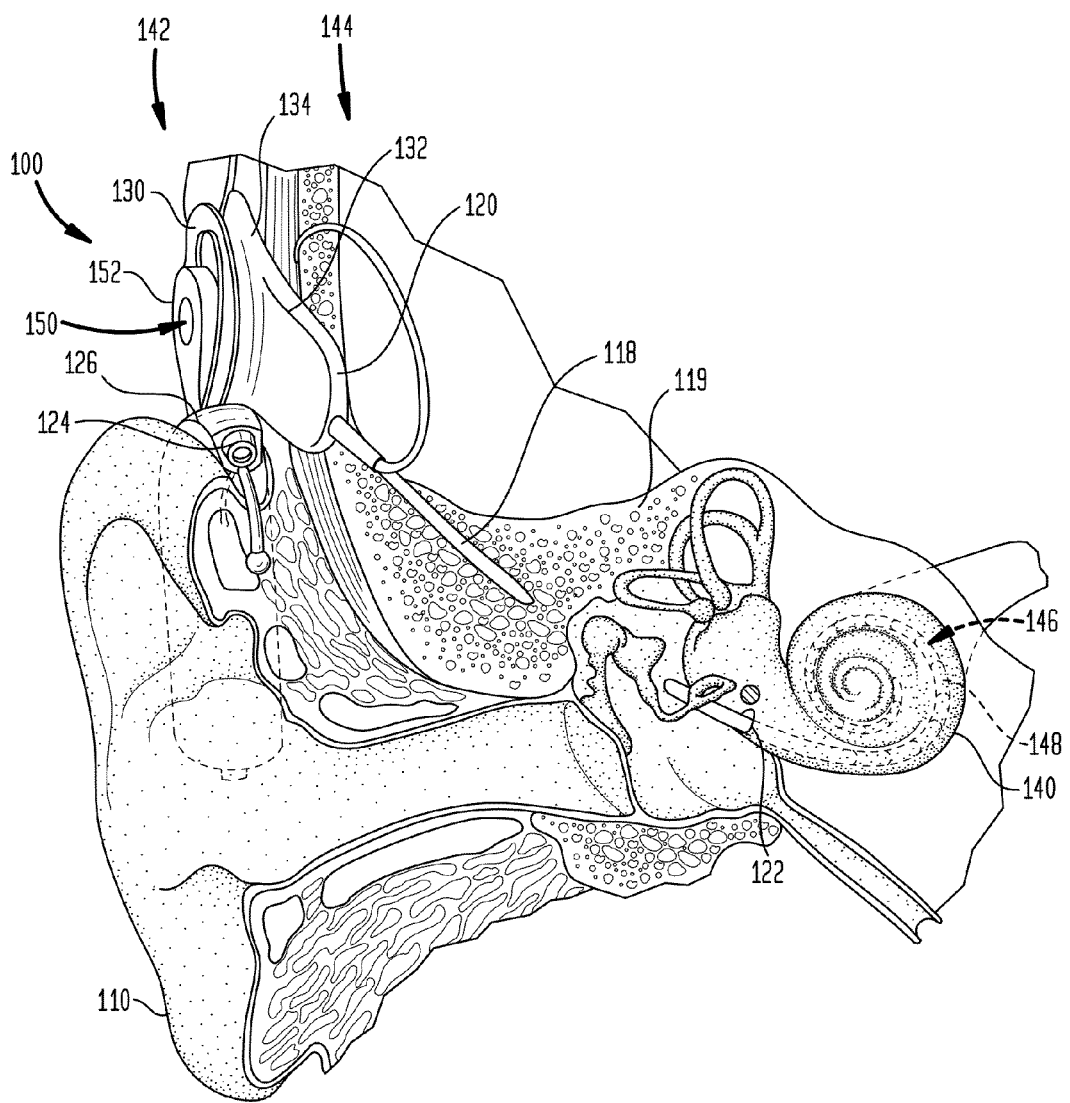
FIG. 1 is a schematic diagram of a cochlear implant that may include a shapeable coil cable in accordance with embodiments of the present invention.

FIG. 1 is perspective view of an exemplary cochlear implant 100 comprising a shapeable coil cable (not shown) in accordance with embodiments of the present invention. In the example of FIG. 1, cochlear implant 100 comprises an external component 142 and an internal or implantable component 144. The external component 142 is directly or indirectly attached to the body of the recipient and typically comprises one or more sound input elements 124 (e.g., microphones, telecoils, etc.) for detecting sound, a sound processor 126, a power source (not shown), and an external coil 130. The sound processor 126 processes electrical signals generated by a sound input element 124 that is positioned, in the depicted embodiment, by auricle 110 of the recipient. The sound processor 126 provides the processed signals to external coil 130 via the shapeable coil cable. Further details of the shapeable coil cable are provided below.

The internal component 144 comprises an elongate stimulating assembly 118, a stimulator unit 120, and an internal receiver and/or transceiver unit 132, referred to simply herein as a transceiver unit 132. Internal transceiver unit 132 and stimulator unit 120 are sometimes collectively referred to herein as a stimulator/transceiver unit and are disposed in a hermetic housing 134. In use, the stimulator/transceiver unit may be positioned in a recess of the temporal bone of the recipient and includes, or is connected to, an internal or implantable coil (not shown). The implantable coil may be configured to receive power and/or data from, and/or transmit power and/or data to, the external coil 130. In certain examples, the external coil 130 transmits electrical signals (e.g., power and stimulation data) to the implantable coil via a radio frequency (RF) link.

Elongate stimulating assembly 118 has a proximal end connected to the stimulator unit 120 and a distal end implanted in cochlea 140. Elongate stimulating assembly 118 also includes a contact array 146 that comprises a plurality of stimulating contacts 148 that may be electrical and/or optical contacts. Stimulating assembly 118 extends from stimulator unit 120 to cochlea 140 through mastoid bone 119 and a cochleostomy 122.

Figure 2A:
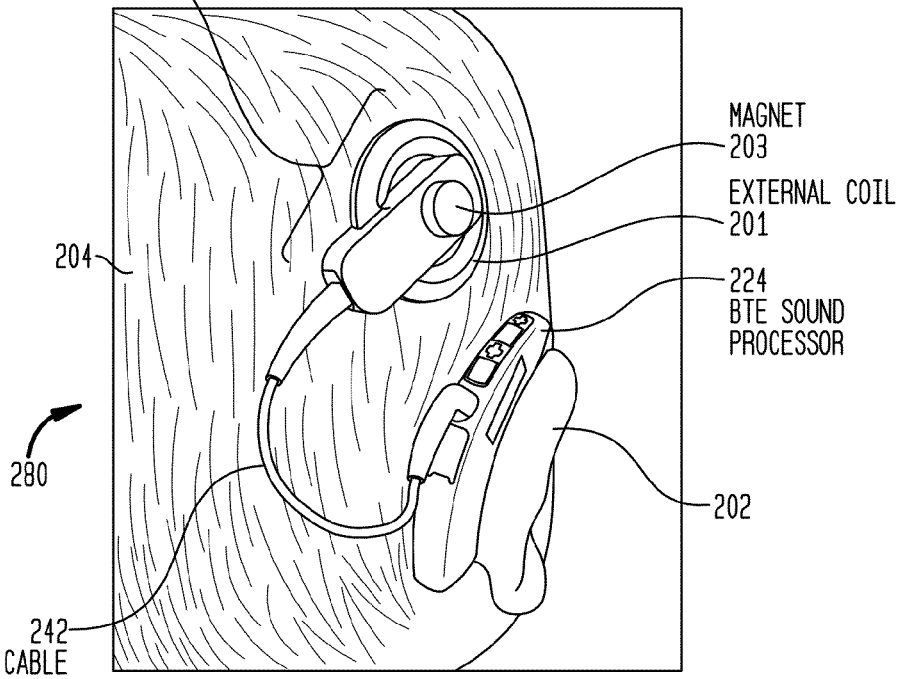
FIGS. 2A and 2B are perspective views of an external component of a cochlear implant that includes a conventional coil cable.
Figure 2B:
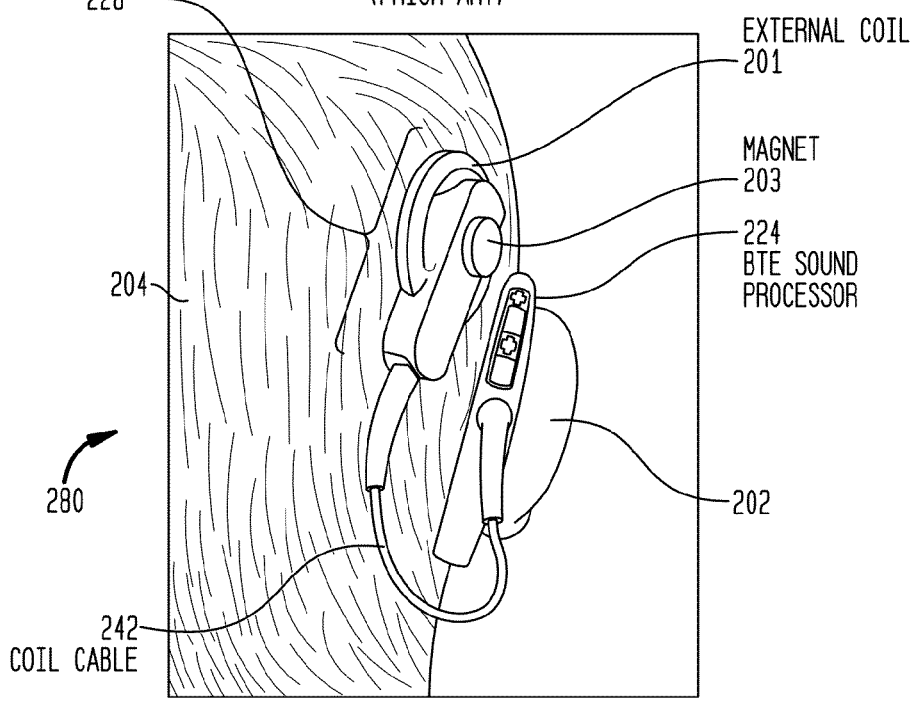

FIGS. 2A and 2B are perspective views of a conventional external component 280 of a cochlear implant. The external component 280 comprises a sound processor 224, an external coil arrangement 228, and a conventional, flexible coil cable 242 electrically connecting the sound processor 224 to the external coil arrangement 228. The sound processor 224 is a behind-the-ear (BTE) sound processor worn on a recipient's ear 202. The external coil arrangement 228 comprises an external coil 201 and a magnet 203. The magnet 203 and the coil 201 may be two standalone parts (i.e., the magnet 203 can be detached from the external coil 901).

In use, the magnet 203 in external coil arrangement 228 is configured to be magnetically coupled to an implantable magnet that is implanted within the recipient's head 204. More specifically, the BTE sound processor 224 is positioned behind the recipient's ear 202 and the external coil arrangement 228 is positioned in close proximity to the implanted magnet. When the external coil arrangement 228 is properly positioned in close proximity to the implanted magnet, the external and implanted magnets will be magnetically coupled so as to secure the external coil arrangement 228 to the recipient's head 204. Additionally, the implanted magnet is positioned within, or in proximity to, an implantable coil. Therefore, when the external and implanted magnets are magnetically coupled, the external coil in the external coil arrangement 228 will be in close proximity to the implantable coil. The close proximity of the external and implantable coils enables the coils to be inductively coupled so data signals and power may be transcutaneously transferred between the coils.

In the arrangement of FIGS. 2A and 2B, the coil cable 242 electrically connects the BTE sound processor 224 to the external coil within external coil arrangement 228. The coil cable 242 is, similar to other conventional coil cables, substantially flexible. Coil cable 242 and other conventional coil cables are made substantially flexible for various reasons. For example, recipients of a cochlear implant may have different shaped and/or sized heads that result in different distances between the location of an implanted magnet and the recipient's ear. As noted, the external coil arrangement is (1) connected to an external device such as a sound processor that is generally positioned on the recipient's ear, but the external coil arrangement should be (2) positioned in close proximity to an implanted magnet. As such, the distance that a coil cable extends between the sound processor and the position in proximity to the implanted magnet may vary from recipient to recipient. Rather than making different length cables for each recipient, manufacturers make the coil cable flexible so that it can span the different lengths needed by different recipients (i.e., account for variations in head sizes and implantable magnet/coil locations).

One problem with the use of flexible coil cables is that, as a result of their flexible nature, a twist is introduced in the cable due to the rotational offset of the external coil arrangement 228 with respect to the BTE sound processor 224. As shown in FIGS. 2A and 2B, this twist in the cable may push the BTE sound processor 224 away from the recipient's head 204. This twist may also result in a substantial portion of the coil cable 242, particularly the mid-point of the cable, extending out from the recipient's head 204 (i.e., a portion of the coil cable 242 is spaced from the recipient's head 204). A large portion of the coil cable 242 being spaced from the recipient's head 204 is aesthetically undesirable and a potential safety hazard since the portion of the cable extending from the head may become caught or snagged on clothing or other objects.

FIGS. 3A and 3B are perspective views of an external component 380 of a cochlear implant in accordance with embodiments of the present invention. External component 380 comprises a BTE sound processor 224 and an external coil arrangement 228 as described above with reference to FIGS. 2A and 2B. However, in the embodiments of FIGS. 3A and 3B, the conventional coil cable 242 (FIGS. 2A and 2B) is replaced by a shapeable coil cable 342 in accordance with embodiments of the present invention. The shapeable coil cable 342 is conformable, non-resilient and configured to maintain an electrical connection between the BTE sound processor 224 and the external coil arrangement 228.

More specifically, the shapeable coil cable 342 has pliability such that a user (e.g., the recipient, a caregiver, a clinician, an audiologist, etc.) can bend or otherwise manipulate the coil cable 342 to have a desired configuration. The configuration set by the user may include, for example, changes in the shape, orientation, and position of the shapeable coil cable. Additionally, the shapeable coil cable 342 has rigidity such that the shapeable coil cable 342 will retain the configuration set by the user.

FIGS. 3A and 3B illustrate the shapeable coil cable 342 in an example configuration set by a user. In this example, when the external coil arrangement 228 and BTE sound processor 224 are worn by a recipient, the user manipulates the shapeable coil cable 342 such that it lies substantially adjacent to the recipient's head 204. That is, the user positions the shapeable coil cable 342 such that substantially the entire cable, particularly a mid-point of the shapeable coil cable, is adjacent to (i.e., in close proximity with) the recipient's head. Due to the non-resilient nature of the shapeable coil cable 342, the coil cable 342 retains this configuration and does not return to its original configuration without the application of an external force, such as another user configuration change.

There is a segment of recipients that have active lifestyles that involve exposure to acceleration or other forces that are sufficient to break the magnetic coupling between an external magnet in an external coil arrangement and an implanted magnet (i.e., the external magnet may become dislodged from the recipient's head). If such a recipient is wearing an external component that includes a conventional flexible coil cable, then the dislodgement of the external magnet may cause the external coil arrangement, the flexible coil, and even possibly the BTE sound processor to fall or fly off the recipient's head. This may cause damage to the device or be painful for the recipient. As such, it is conventional practice to reduce the risk of the external coil arrangement from falling off during active physical activities through the use of stronger external and/or implantable magnets. However, the use of stronger magnets increases the amount of pressure exerted on the recipient's skin, which may induce discomfort and may increase the risk of skin narcosis.

In certain embodiments, the shapeable coil cable 342 is configured to eliminate the need for stronger magnets to reduce the risk of the external coil arrangement from flying/falling off the recipient's head 204. More particularly, the shapeable coil cable 342 may have rigidity such that not only does the shapeable coil cable 342 retain the configuration set by a user, but the shapeable coil cable 342 also helps to retain the external coil arrangement 228 at a position in proximity to the implanted magnet upon the application of certain external forces.

Figure 4A:
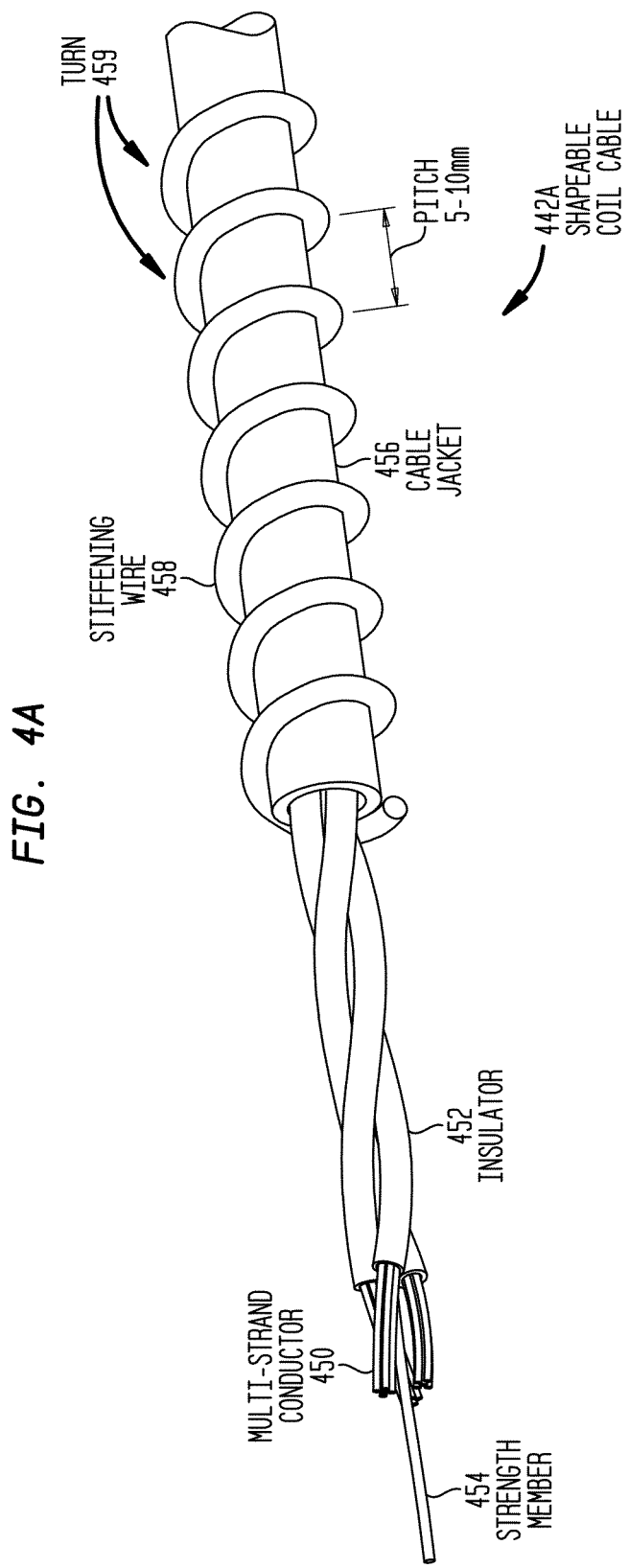
FIG. 4A is a perspective view of a shapeable coil cable in accordance with embodiments of the present invention.

FIG. 4A is a perspective view of a portion of a shapeable coil cable 442A in accordance with embodiments of the present invention. The center of shapeable coil cable 442A comprises a strength member 454 that is configured to resist tensile forces placed on the cable. Although resistive to tensile forces, the strength member 454 is substantially flexible and does not add any stiffening characteristics to the cable 442. In certain embodiments, the strength member 454 is formed from aramid fiber.

As shown in FIG. 4A, a plurality of elongate conductors 450 is wound around the strength member 454. The elongate conductors 450 extend the length of the shapeable coil cable 442A so as to carry electrical signals between connectors (not shown) disposed at the opposing ends of the cable. The elongate conductors 450 are each multi-strand conductors disposed in respective insulating coverings (insulators) 452. For ease of illustration, a portion of the elongate conductors 450 have been omitted from FIG. 4A to illustrate the underlying strength member 454. Similarly, a portion of the insulators 452 have been omitted from FIG. 4A to illustrate the multi-strand conductors 450.

In the specific embodiment of FIG. 4A, three elongate conductors 450 are wound around the strength member 454. It is to be appreciated that fewer or greater numbers of elongate conductors 450 may be used in alternative embodiments of the present invention. Similarly, alternative embodiments may include single strand conductors, rather than the multi-strand conductors.

The shapeable coil cable 442A also comprises a flexible cable jacket 456 that is disposed around the elongate conductors 450. In general, the cable jacket 456 extends the length of the shapeable coil cable 442A between the connectors. However, a portion of the cable jacket 456 has been omitted form FIG. 4A.

In the embodiments of FIG. 4A, a stiffening element 458 is added to the cable jacket 456. The stiffening element 458 is a stiffening wire that is co-axially wound around the cable jacket 456. The stiffening wire 458 has an arrangement (i.e., material properties, diameter, wind spacing, etc.) so as to make the shapeable coil cable 442A selectively conformable and non-resilient. That is, the stiffening wire 458 provides the shapeable coil cable with sufficient pliability such that it can be shaped by a user and with sufficient rigidity such that the cable it will retain the shape set by the user.

The stiffening wire 458 may have a number of different arrangements that depend on a desired pliability and/or rigidity of the shapeable coil cable 442A. In certain embodiments, the stiffening wire 458 is made from an Iron, Nickel, Cobalt alloy (e.g., Kovar) or a Nickel and Copper alloy (e.g., Monel). The stiffening wire 458 may be uncoated or coated (insulated) with Polyvinyl chloride (PVC) or polyamide (nylon). In certain embodiments, the stiffening wire 458 may have a diameter in the range of approximately 0.38 millimeters to approximately 0.51 millimeters. The stiffening wire 458 may have hardness in the range of approximately 70 Rockwell B Hardness (HRB) to approximately 80 HRB. The stiffening wire 458 may have an elastic modulus in the range of approximately 160 gigapascal (GPa) to approximately 180 GPa.

Stiffening wire 458 is co-axially wound around cable jacket 456 so as to form a plurality of turns 459. The number of turns 459 of the stiffening wire 458, as well as the pitch of the turns, may affect the pliability and rigidity of the shapeable coil cable 442A. In certain embodiments, two adjacent turns have a pitch in the range of approximately five (5) millimeters to approximately ten (10) millimeters.

As noted, FIG. 4A illustrates an arrangement where the stiffening element 458 is a stiffening wire that is co-axially wound around the outside of cable jacket 456. It is to be appreciated that the stiffening element may have alternative arrangements. For example, FIG. 4B illustrates an alternative embodiment in which a shapeable coil cable 442B comprising a plurality of stiffening elements 461A and 461B. In the embodiments of FIG. 4B, the stiffening elements 461A and 461B are wires that are attached to the cable jacket 456 via an adhesive 463, or alternatively integrally molded with cable jacket 456. The stiffening wires 461A and 461B each have a substantially straight orientation and are disposed on opposing sides of the cable jacket 456. Similar to the embodiments of FIG. 4A, the stiffening wires 461A and 461B collectively have an arrangement (i.e., material properties, diameter, relative positions, etc.) so as to make the shapeable coil cable 442B selectively conformable and non-resilient. The stiffening wires 461A and 461B may be formed from the same or different materials as described with reference to FIG. 4A.

FIG. 5 is a side view of the shapeable coil cable 442A in use as part of an external arrangement 480 of a cochlear implant. As shown, the shapeable coil cable 442A has a first end terminating at a connector 462 connected to an external coil arrangement 428. Similar to the above examples, external coil arrangement 428 comprises a housing 466 in which an external coil 472 and a magnet 468 are disposed. Several portions of the housing 466 have been omitted from FIG. 5 to illustrate the external coil 472 and the magnet 468.

The shapeable coil cable 442A also has a second end terminating at connector 464 connected to a BTE sound processor 424. The BTE sound processor 424 is attached to an earhook 425 such that the BTE sound processor 424 is worn on the ear 402 of a recipient.

Figure 6A:
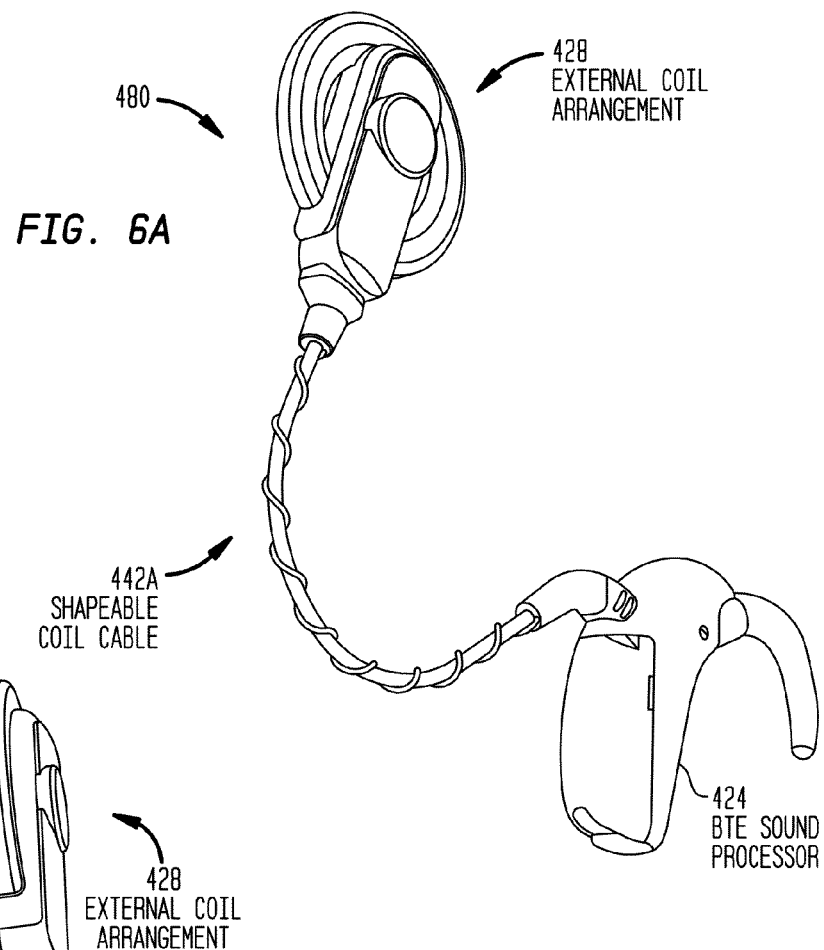
FIGS. 6A and 6B are perspective views of the external arrangement of FIG. 5.
Figure 6B:
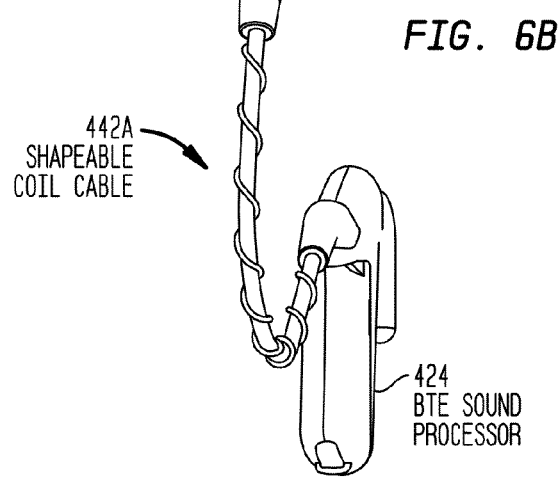

In the example of FIG. 5, the connector 462, conductors 450 in shapeable coil cable 442A, and connector 464 provide an electrical connection between the BTE sound processor 424 and external coil arrangement 428, namely external coil 472. As noted above, the shapeable coil 442A is conformable such that a user may shape and position the cable against the head 404 of the recipient. The shapeable coil 442A is also non-resilient such that it remains in the shape and position set by the user FIGS. 6A and 6B are perspective views of external arrangement 480. For ease of illustration, the shapeable coil cable 442A, BTE sound processor 424, and external coil arrangement 428 are shown separate from a recipient's head.

Figure 7:
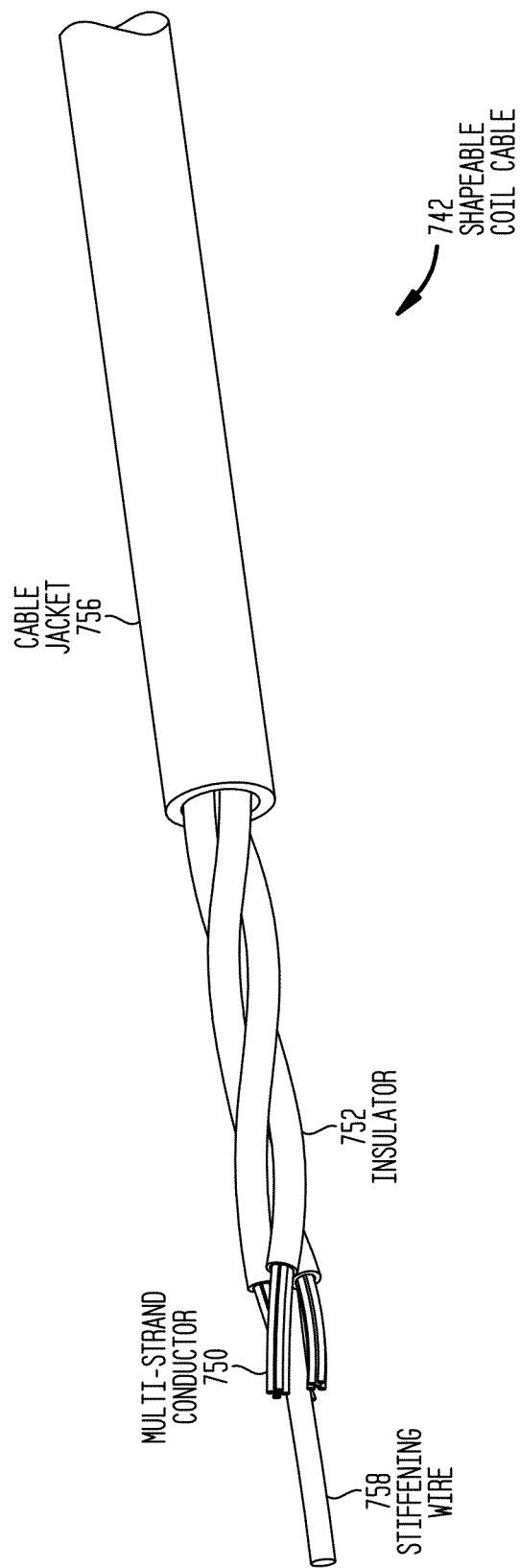
FIG. 7 is a perspective view of a shapeable coil cable in accordance with further embodiments of the present invention.

FIG. 7 is a perspective view of a portion of a shapeable coil cable 742 in accordance with alternative embodiments of the present invention. The shapeable coil cable 742 comprises a plurality of wound elongate conductors 750 that extend the length of the shapeable coil cable 742 so as to carry electrical signals between two connectors (not shown) disposed at the opposing ends of the cable. The elongate conductors 750 are each multi-strand conductors disposed in respective insulating coverings (insulators) 752. For ease of illustration, a portion of the insulators 752 have been omitted from FIG. 7 to illustrate the multi-strand conductors 750.

In the specific embodiment of FIG. 7, the shapeable coil cable 742 comprises three wound elongate conductors 750. It is to be appreciated that fewer or greater numbers of elongate conductors 750 may be used in alternative embodiments of the present invention. Similarly, alternative embodiments may include single strand conductors, rather than the multi-strand conductors.

The shapeable coil cable 742 also comprises a flexible cable jacket 756 that is disposed around the elongate conductors. In general, the cable jacket 756 extends the length of the cable between the connectors. A portion of the cable jacket 756 has been omitted form FIG. 7.

In the embodiments of FIG. 7, the center of shapeable coil cable 742 comprises a stiffening element 758. The stiffening element 758 is a stiffening wire around which the elongate conductors 750 are wound. The stiffening wire 758 has an arrangement (i.e., material properties, diameter, etc.) so as to make the shapeable coil cable 742 selectively conformable and non-resilient. That is, the stiffening wire 758 provides the shapeable coil cable with sufficient pliability such that it can be shaped by a user and with sufficient rigidity such that the cable it will retain the shape set by the user.

The stiffening wire 758 may have a number of different arrangements that depend on a desired pliability and/or rigidity of the shapeable coil cable 742. In certain embodiments, the stiffening wire 758 is an Iron, Nickel, Cobalt alloy (e.g., Kovar) or a Nickel and Copper alloy (e.g., Monel). The stiffening wire 758 may be uncoated or coated (insulated) with Polyvinyl chloride (PVC) or polyamide (nylon). In certain embodiments, the stiffening wire 458 may have a diameter in the range of approximately 0.25 millimeters to approximately 0.32 millimeters. The stiffening wire 458 may have hardness in the range of approximately 70 HRB to approximately 80 HRB. The stiffening wire 758 may have an elastic modulus in the range of approximately 160 GPa to approximately 180 GPa.

Figure 8:
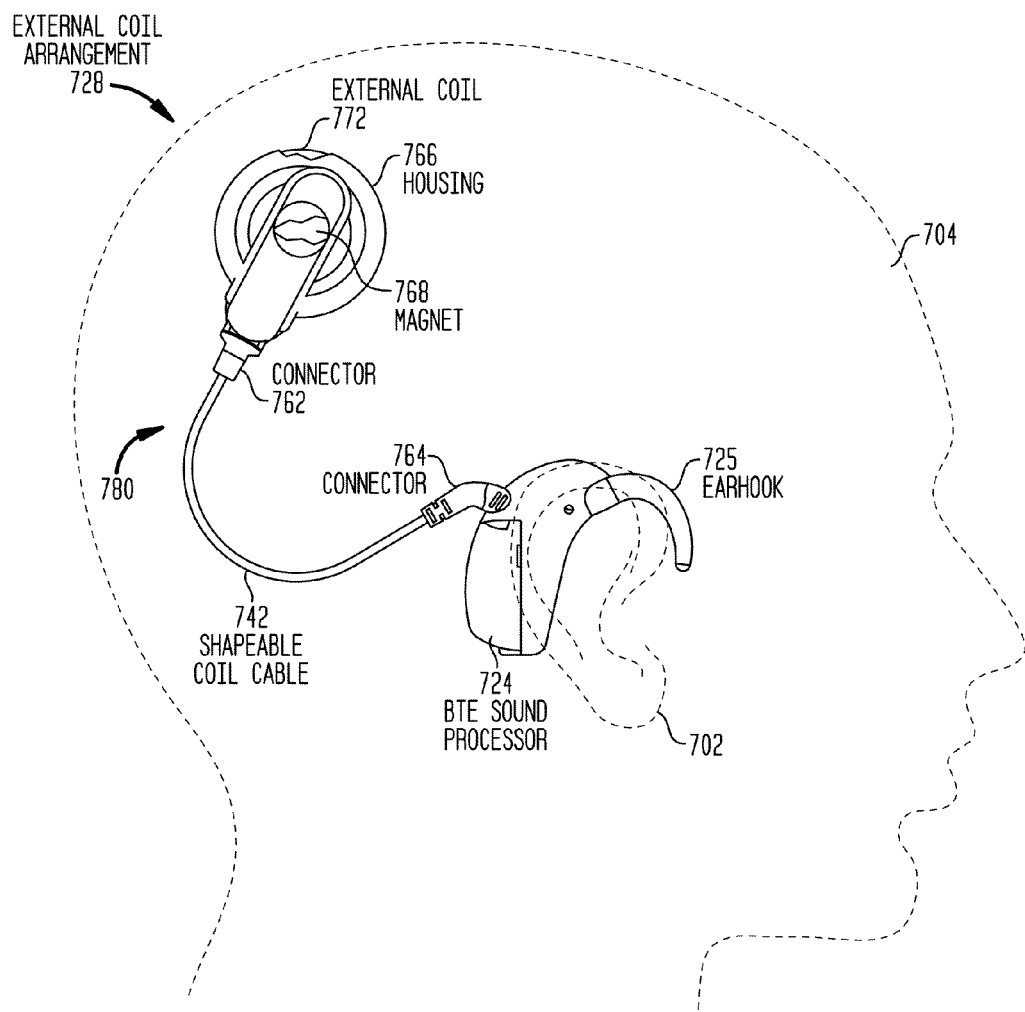
FIG. 8 is a side view of an external component of a cochlear implant that comprises a shapeable coil cable in accordance with embodiments of the present invention.

FIG. 8 is a side view of the shapeable coil cable 742 in use as part of an external arrangement 780 of a cochlear implant. As shown, the shapeable coil cable 742 has a first end terminating at a connector 762 connected to an external coil arrangement 728. Similar to the above examples, external coil arrangement 728 comprises a housing 766 in which an external coil 772 and a magnet 768 are disposed. Several portions of the housing 766 have been omitted from FIG. 8 to illustrate the external coil 772 and the magnet 768.

The shapeable coil cable 742 also has a second end terminating at connector 764 connected to a BTE sound processor 724. The BTE sound processor 724 is attached to an earhook 725 such that the BTE sound processor 724 is worn on the ear 702 of a recipient.

In the example of FIG. 8, the connector 762, conductors 750 in shapeable coil cable 742, and connector 764 provide an electrical connection between the sound processor 724 and external coil arrangement 728, namely external coil 772. As noted above, the shapeable coil 742 is conformable such that a user may shape and position the cable against the head 704 of the recipient. The shapeable coil 742 is also non-resilient such that it remains in the shape and position set by the user FIGS. 9A and 9B are perspective views of external arrangement 780. For ease of illustration, the shapeable coil cable 742, BTE sound processor 724, and external coil arrangement 28 are shown separate from a recipient's head.

FIG. 10 is a flowchart of a method 1000 for manufacturing a shapeable coil cable in accordance with embodiments of the present invention. Method 1000 begins at 1002 where a plurality of elongate conductors is wound together. In certain embodiments, the elongate conductors are wound around a strength member. At 1004, an elongate cable jacket is positioned around the wound elongate conductors. At 1006, an elongate stiffening wire is co-axially wound around the cable jacket.

FIG. 11 is a flowchart of a method 1100 for manufacturing a shapeable coil cable in accordance with alternative embodiments of the present invention. Method 1100 begins at 1102 where a plurality of elongate conductors is wound around an elongate stiffening wire. At 1104, an elongate cable jacket is positioned around the wound elongate conductors.

FIG. 12 is a flowchart of a method 1200 in accordance with embodiments of the present invention. Method 1200 begins at 1202 where a first end of a non-resilient shapeable coil cable is connected to an external coil arrangement that is configured to be magnetically coupled to an implantable magnet implanted in a recipient. In certain embodiments, the first end of the shapeable coil cable includes a connector that is configured to mate with a connector slot of the external coil arrangement.

At 1204, a second end of the shapeable coil cable is connected to a sound processor configured to be worn on the ear of the recipient. In certain embodiments, the second end of the shapeable coil cable includes a connector that is configured to mate with a connector slot of the sound processor.

At 1206, the sound processor is positioned on the ear of the recipient and at 1208 the external coil arrangement is positioned at a location so as to be magnetically coupled to the implantable magnet implanted in the recipient. At 1210, the shapeable coil cable is manipulated to a desired configuration in which a mid-point of the shapeable coil cable is substantially adjacent to the recipient's head. The shapeable coil cable is configured to retain this desired configuration.

As noted, embodiments of the present invention are generally directed to a shapeable coil cable that is conformable and non-resilient. The shapeable coil cable in accordance with embodiment of the present invention has several advantages over conventional flexible coil cables. For example, a flexible coil cable mechanically decouples the external coil arrangement from the sound processor. Such a decoupled system behaves as two mechanical parts that are independently mounted on the ear (the sound process) and hanging on an implanted magnet (external coil arrangement). However, a shapeable coil cable as described herein mechanically couples the sound processor to the external coil arrangement. Such a complete system is mechanically more stable than conventional arrangements since the system behaves as one rigid body with multiple mechanical anchor points (sound processor sitting on the ear and the magnet in the external coil arrangement) spread across a wider surface area. The mechanically coupled system provided by the shapeable coil cable may be analogous to a tripod where the further spread the attachment points (legs), the more stable the system becomes.

Additionally, the shapeable coil cable as described herein increases the comfort associated with a worn external arrangement. In particular, because the external coil arrangement is partially supported by the rigid coil, clinicians/surgeons can use smaller or lower strength implantable and/or external magnets in order to minimize discomfort and risk of skin necrosis.

Furthermore, shapeable coil cable as described herein increases the discreteness of a worn external arrangement. As noted, a user can shape and position the shapeable coil cable such that it is rested against the recipient's scalp and prevent it from sticking out from the hair or the head. Similarly, with the coil cable rested on the scalp, there is less risk of the coil cable accidentally getting caught and falling or flying off the recipient's head.

Finally, the shapeable coil cable as described herein may increase the battery life of the external sound processor. More particularly, the shapeable coil cable could potentially provide more effective electrical shielding than a flexible coil cable. This more effective shielding enables a reduction in electromagnetic suppression measures implemented in the coil, which would improve power efficiency of the inductive link while still in compliance with electromagnetic standards.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A hearing prosthesis, comprising:
    an implantable component configured to be implanted in a recipient; and
    an external component comprising:
        a sound processor configured to be worn by a recipient,
        an external coil arrangement, and
        a non-resilient shapeable cable configured to maintain an electrical connection between the sound processor and the external coil arrangement, wherein the shapeable cable has sufficient pliability to accept a configuration set by a user and sufficient rigidity to support the external coil arrangement at a set position when the sound processor element is worn by the recipient, wherein the shapeable cable comprises:
        a plurality of elongate conductors,
        an elongate cable jacket disposed around the elongate conductors, and
        an elongate stiffening wire co-axially wound around the cable jacket.

2. The hearing prosthesis of claim 1, wherein the implantable component comprises:
    an implantable magnet; and
    an implantable inductive coil.

3. The hearing prosthesis of claim 2, wherein external coil arrangement comprises:
    a housing;
    an external inductive coil disposed in the housing and configured to transcutaneously transfer electrical signals to the implantable inductive coil; and
    an external magnet disposed in the housing and configured to be magnetically coupled to an implantable magnet.

4. The hearing prosthesis of claim 1, wherein the hearing prosthesis is a cochlear implant.

5. A method comprising:
    connecting a first end of a non-resilient shapeable coil cable to an external coil arrangement of a hearing prosthesis, wherein the external coil arrangement is configured to be magnetically coupled to an implantable magnet implanted in a recipient and wherein the cable comprises an elongate stiffening wire, a plurality of elongate conductors wound around the elongate stiffening wire, and an elongate cable jacket disposed around the elongate conductors;
    connecting a second end of the shapeable coil cable to a sound processor configured to be worn on the ear of the recipient;
    positioning the sound processor on the ear of the recipient;
    positioning the external coil arrangement at a location so as to be magnetically coupled to the implantable magnet implanted in the recipient;
    manipulating the shapeable coil cable to a desired configuration in which a mid-point of the shapeable coil cable is substantially adjacent to the recipient's head, wherein the shapeable coil cable has sufficient rigidity to support the external coil arrangement at a set position when the sound processor element is worn on the ear of the recipient; and
    stimulating the ear of the recipient with the hearing prosthesis.

6. The method of claim 5, wherein the external coil arrangement comprises:
    a housing;
    an external inductive coil disposed in the housing and configured to transcutaneously transfer electrical signals to the implantable inductive coil; and
    an external magnet disposed in the housing and configured to be magnetically coupled to an implantable magnet.

7. The method of claim 5, wherein the implantable component comprises:
    an implantable magnet; and
    an implantable inductive coil.

8. The method of claim 5, wherein the hearing prosthesis is a cochlear implant.

9. A hearing prosthesis, comprising:
    an implantable component configured to be implanted in a recipient; and
    an external component comprising:
        a sound processor configured to be worn by a recipient,
        an external coil arrangement, and
        a non-resilient shapeable cable configured to maintain an electrical connection between the sound processor and the external coil arrangement, wherein the shapeable cable has sufficient pliability to accept a configuration set by a user and sufficient rigidity to support the external coil arrangement at a set position when the sound processor element is worn by the recipient, wherein the shapeable cable comprises:
an elongate stiffening wire,
a plurality of elongate conductors wound around the elongate stiffening wire, and
an elongate cable jacket disposed around the elongate conductors.

10. The hearing prosthesis of claim 9, wherein the implantable component comprises:
an implantable magnet; and
an implantable inductive coil.

11. The hearing prosthesis of claim 9, wherein external coil arrangement comprises:
a housing;
an external inductive coil disposed in the housing and configured to transcutaneously transfer electrical signals to the implantable inductive coil; and
an external magnet disposed in the housing and configured to be magnetically coupled to an implantable magnet.

12. The hearing prosthesis of claim 9, wherein the hearing prosthesis is a cochlear implant.

* * * * *